US00PP29526P3

(12) United States Plant Patent
O'Connell

(10) Patent No.: US PP29,526 P3
(45) Date of Patent: Jul. 17, 2018

(54) ***ECHEVERIA* PLANT NAMED 'RUBY KISSED'**

(50) Latin Name: *Echeveria hybrida*
Varietal Denomination: Ruby Kissed

(71) Applicant: Renee O'Connell, Escondido, CA (US)

(72) Inventor: Renee O'Connell, Escondido, CA (US)

(73) Assignee: Altman Specialty Plants Inc., Vista, CA (US)

( * ) Notice: Subject to any disclaimer, the term of this patent is extended or adjusted under 35 U.S.C. 154(b) by 0 days.

(21) Appl. No.: 15/330,711

(22) Filed: Oct. 27, 2016

(65) Prior Publication Data

US 2018/0124983 P1 May 3, 2018

(51) Int. Cl.
*A01H 5/02* (2018.01)
*A01H 5/12* (2018.01)

(52) U.S. Cl.
USPC ..... Plt./373
CPC ..... *A01H 5/12* (2013.01)

(58) Field of Classification Search
USPC ..... Plt./373
See application file for complete search history.

(56) References Cited

PUBLICATIONS https://www.flickr.com/photos/echeverian/17323501299/. 2015.*

* cited by examiner

*Primary Examiner* — Annette H Para
(74) *Attorney, Agent, or Firm* — Cassandra Bright

(57) ABSTRACT

A new and distinct *Echeveria* cultivar named 'Ruby Kissed' is disclosed, characterized by chunky green-greyed-green foliage forming dense rosettes. Plants are compact and produce offsets prolifically, useful for many pot sizes. The new variety is an *Echeveria*, part of the Crassulaceae complex that includes *Pachyphytum, Graptopetalum, Sedum, Crassula* and others. *Echeveria* is a popular genus, typically produced as container plants or landscape plants. Currently, there is a growing use of *Echeveria* for artistic creations such as wedding bouquets, table centerpieces and other ornamental uses for social occasions.

1 Drawing Sheet

Latin name of the genus and species: *Echeveria hybrida*.
Variety denomination: 'RUBY KISSED'.

BACKGROUND OF THE INVENTION

The new *Echeveria* cultivar is the product of a planned breeding program. The new variety originated from a cross pollination of the proprietary, unpatented, seed parent, *Echeveria* 'Cris' with the pollen parent, an unpatented, proprietary variety of *Echeveria* referred to as 'Maz 01'. The crossing was made during March of 2012 at a commercial greenhouse in Vista, Calif.

'Ruby Kissed' was discovered by the inventor, Renee O'Connell, in August 2013, in Vista, Calif. at a commercial greenhouse in Vista, Calif.

Asexual reproduction of the new cultivar 'Ruby Kissed' was first performed in Vista, Calif., at a commercial greenhouse by vegetative cuttings in September 2013. 'Ruby Kissed' has since produced multiple generations and has shown that the unique features of this cultivar are stable and reproduced true to type.

SUMMARY OF THE INVENTION

The cultivar 'RUBY KISSED' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RUBY KISSED'. These characteristics in combination distinguish 'RUBY KISSED' as a new and distinct *Echeveria* cultivar:

1. Dense rosettes of chunky green/greyed-green leaves.
2. Foliage apex colored greyed-purple in high light conditions.
3. Chunky and compact morphology filling a 9 cm pot with a single cutting.
4. Prolifically produces offsets, forming multiple-headed cluster that are aesthetically pleasing.
5. Versatility of use, due to prolific offsetting, useful for small pot sizes as well as pot sizes more than 8 inches in diameter.
6. Coloration and plant shape useful for mixed succulent groupings.

PARENTAL COMPARISON

Plants of the new cultivar 'RUBY KISSED' are similar to plants of the seed parent, in most horticultural characteristics, however, plants of the new cultivar 'RUBY KISSED' differ in the following;

1. 'Ruby Kissed' forms blue-green rosettes, tipped with greyed-purple, whereas *Echeveria* 'Cris', while similar in overall rosette color, does not exhibit the dark tipped leaves of *Echeveria* 'Ruby Kissed'.
2. *Echeveria* 'Ruby Kissed' forms larger rosettes than does *Echeveria* 'Cris', decreasing production time when planted in a larger pot, such as an 8" bulb pan.

3. *Echeveria* 'Cris' is suitable for 2.5 inch and 9 cm pot sizes. *Echeveria* 'Ruby Kissed' can also be used in 2.5" and 9 cm pot sizes, and additionally can be used in quart, 5", 6" and 8" pots. The seed parent is far less prolific in producing plantlets from leaf cuttings and does not fill larger pots as easily.

Plants of the new cultivar 'RUBY KISSED' are similar to plants of the pollen parent, in most horticultural characteristics, however, plants of the new cultivar 'RUBY KISSED' differ in the following;

1. The new variety is more prolifically producing offsets than the pollen parent.
2. Freely offsets, enhancing production and creating an attractive cluster, whereas the pollen parent offsets only occasionally.
3. 'Ruby Kissed' forms blue-green rosettes, tipped with greyed-purple, whereas the pollen parent, produces blue colored rosettes.

COMMERCIAL COMPARISON

Plants of the new cultivar 'RUBY KISSED' are comparable to the unpatented, commercial variety *Echeveria minima*. The two varieties are similar in most horticultural characteristics; however, the new variety 'RUBY KISSED' differs in the following:

1. 'Ruby Kissed' produces offsets much more prolifically than this comparator.
2. Foliage color of the new variety is green-blue, foliage color of this comparator is blue.
3. The new variety grows much faster than plants of this comparator, produces a commercial product much faster.
4. Plants of the new variety produce larger rosettes than plants of this comparator, allowing for production in large pot sizes.

Plants of the new cultivar 'RUBY KISSED' can also be comparable to the unpatented commercial variety *Echeveria* 'Azulita'. The two *Echeveria* varieties are similar in most horticultural characteristics; however, the new variety 'RUBY KISSED' differs in the following:

1. Foliage color of the new variety is green-blue, foliage color of this comparator is icy blue.
2. 'Ruby Kissed' produces offsets much more prolifically than this comparator.
3. The new variety grows much faster than plants of this comparator, produces a commercial product much faster.
4. Plants of the new variety produce larger rosettes than plants of this comparator, allowing for production in large pot sizes.

BRIEF DESCRIPTION OF THE PHOTOGRAPH

The accompanying photograph in illustrates in full color a freely offsetting plant of *Echeveria* 'Ruby Kissed', grown in a greenhouse in Vista, Calif. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2007 except where general terms of ordinary dictionary significance are used. The following observations and measurements describe 'Autumn Flame' plants in a commercial greenhouse in Vista, Calif. Temperatures ranged from approximately 10° C. to 38° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Echeveria hybrida* 'RUBY KISSED'.

PROPAGATION

Type of propagation typically used: Terminal vegetative divisions, offsets.

Time to initiate roots: About 14 days at approximately 22° C.

Root description: Fibrous, brown, not accurately measured with a color chart.

PLANT

Age of plant described: Approximately 4 months from cutting.

Container size of the plant described: 8 inch.

Growth habit: Densely rosulate, mounding.

Height: Approximately 9.0 cm to top of highest leaf. Approximately 35 cm to top of highest inflorescence.

Plant spread: 22 cm.

Growth rate: Moderately fast.

Branching characteristics: Freely offsetting. Approximately 8 to 12 offsets on a plant of this size and age.

FOLIAGE

Leaf:

*Arrangement*.—Rosulate.

*Average length*.—Approximately 3.0 cm.

*Average width*.—Approximately 1.3 cm.

*Width at base*.—0.8 cm.

*Average depth*.—Approximately 4 to 6 mm.

*Shape of blade*.—Spatulate, with overall apical shape somewhat angular and sloping.

*Apex*.—Mucronate.

*Base*.—Cuneate.

*Margin*.—Rounded.

*Texture of top surface*.—Glabrous, glaucous.

*Texture of bottom surface*.—Glabrous, glaucous.

*Quantity of leaves per rosette*.—Approximate range of 80 to 120.

*Color*.—Young foliage upper side: Near RHS Green 136C, base near Greyed-Green 192D. Young foliage, under side: Near RHS Greyed-Green 191B, base near White 155A. Mature foliage, upper side: Near RHS Green 137B, covered in a glaucous layer near Greyed-Green 188C. Base near Yellow-Green 144D, with glaucous layer 188C. Apex, on mucronation Greyed-Purple 187B. Mature foliage, under side: Near RHS Green 138C, very light glaucous layer near 188D. Base Green 138D. Apex, on mucronation Greyed-Purple 187B.

*Venation*.—There is no visual appearance of venation.

FLOWER

Natural flowering season: Spring, Summer, irregularly.

Inflorescence type and habit: Lateral, bifurcate.

Rate of flower opening: 1 to 3 flowers open every 5 to 7 days, depending upon ambient conditions.

Flower longevity on plant: 2-3 days, depending upon ambient conditions.

Quantity of flowers: 20 to 40.

*Total inflorescence size*.—Height: Approximately 35 cm. Width: Approximately 6.9 cm.

*Corolla*.—Arrangement: 5-merous, the outer petals spreading to recurved. Size: Length: Approximately 1.1 cm. Width: Approximately 0.5 cm at widest point. Lobe Length: Approximately 2.1 mm. Lobe width: Approximately 3 mm.

*Margin*.—Entire.

*Shape*.—Narrow deltate.

*Apex*.—Acute.

*Base*.—Fused, approximately 90% of length.

*Texture*.—Glabrous.

Petal color:

*When opening*.—Petal color, outer surface: Near RHS Orange 32A, apex Yellow-Orange 16B. Petal color, interior: Not visible until flower matures.

Petal color:

*Fully opened*.—Outer surface: Near RHS Orange-Red 33B, heavily streaked 16C. Inner surface: Near RHS 16C, flushed 33B.

*Color changes when aging*.—Outer surface darkens to 34A, interior remains 16C. Bud: (near opening): Shape: Conical. Length: Approximately 0.9 cm. Diameter: Approximately 0.4 cm. Color: Near RHS Orange-Red 34C.

*Sepals*.—Length of sepal: Approximately 0.6 cm long. Width of sepal: Approximately 0.2 cm at widest point. Color outer surface: Near RHS Green 138B. Color inner surface: Near RHS Green 138A.

*Peduncle*.—Length: Average range 20 to 30 cm. Width: Approximately 0.6 cm. Strength: Weak, floppy to moderately strong. Texture: Glabrous. Color: Near RHS Greyed-Red 185C, irregular glaucous covering near Greyed-Purple N187D.

*Pedicels*.—Length: Approximately 0.4 to 0.6 cm. Width: Approximately 0.2 cm. Aspect: Straight. Strength: Moderately strong. Color: Near RHS Orange-Red 34D.

*Fragrance*.—None detected.

REPRODUCTIVE ORGANS

Stamens:

(*Androecium*).—Number: Average 10. Filament Length: Approximately 0.5 cm. Filament Color: Near RHS White N155C. Anther length: 0.1 cm. Anther Color: Near RHS Yellow 12C. Anther Shape: Oblong. Pollen Color: Near RHS Yellow 12D. Pollen quantity: Scant.

Pistil:

(*Gymnoecium*).—Number: Average 5. Length: Approximately 0.9 cm. Style Color: Near Green-Yellow 1B. Style length: Approximately 0.4 cm. Stigma: Shape: Linear. Color: Near Yellow-Green 144C. Ovary Color: Near RHS Yellow-Orange 14D.

OTHER CHARACTERISTICS

Fruits and seeds: Typical to Genus. Minute, less than 1 mm dry seeds. Colored between black and brown, too small to accurately measure with color chart.

Temperature tolerance: Tolerates temperatures from approximately −2° C. to at least 35° C.

Disease/pest resistance: More resistance to the pathogen known as *Fusarium*, a typical disease of *Echeveria*, has been observed. Neither resistance nor susceptibility to normal pests of *Echeveria*, which include thrips and aphid.

Drought tolerance: Tolerates at least 3 weeks of high temperatures without supplemental water, showing no serious damage to plant.

What is claimed is:

1. new and distinct cultivar of *Echeveria* plant named 'RUBY KISSED' as herein illustrated and described.

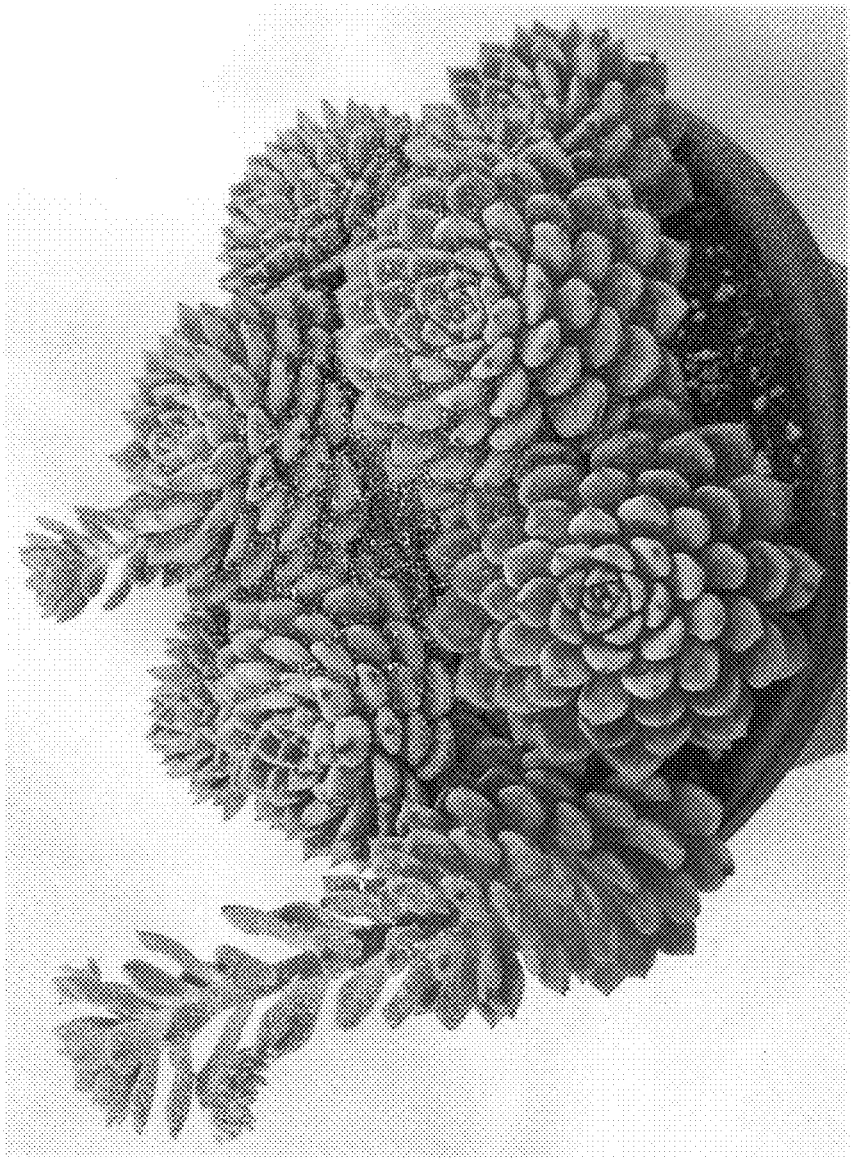

* * * * *